United States Patent [19]

Seybold

[11] Patent Number: 4,464,284

[45] Date of Patent: Aug. 7, 1984

[54] MIXTURES OF OPTICAL BRIGHTENERS

[75] Inventor: Guenther Seybold, Ludwigshafen, Fed. Rep. of Germany

[73] Assignee: BASF Aktiengesellschaft, Ludwigshafen, Fed. Rep. of Germany

[21] Appl. No.: 428,339

[22] Filed: Sep. 29, 1982

Related U.S. Application Data

[62] Division of Ser. No. 214,227, Dec. 8, 1980, Pat. No. 4,380,514.

[30] Foreign Application Priority Data

Jan. 12, 1980 [DE] Fed. Rep. of Germany ....... 3001065

[51] Int. Cl.$^3$ .................. C09K 11/06; C07C 119/048
[52] U.S. Cl. ........................... 252/301.21; 260/465 H
[58] Field of Search ...................... 252/301.21, 301.24, 252/301.16; 260/465 H

[56] References Cited

U.S. PATENT DOCUMENTS 4,330,427  5/1982  Martini et al. ................. 252/301.24
4,336,155  6/1982  Martini et al. ................. 252/301.21
4,380,514  4/1983  Seybold ......................... 260/465 H

FOREIGN PATENT DOCUMENTS 30917    12/1980  European Pat. Off. ....... 252/301.21
0023027   1/1981  European Pat. Off. .
920988    3/1963  United Kingdom ........... 252/301.21
1045443  10/1966  United Kingdom .

Primary Examiner—Howard S. Williams
Assistant Examiner—T. L. Williams
Attorney, Agent, or Firm—Oblon, Fisher, Spivak, McClelland & Maier

[57] ABSTRACT

A mixture of optical brightener compounds consisting of a compound of formula (A)

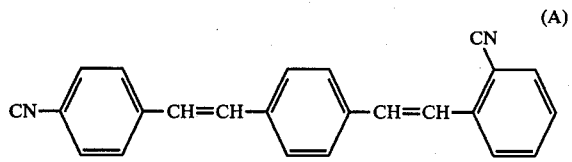

(A)

and at least one compound of formula (B) or (C) where formula (B) is

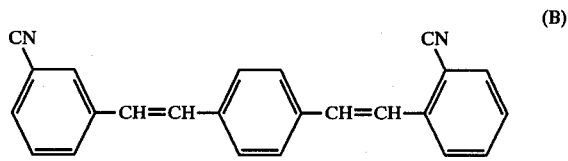

(B)

and formula (C) is

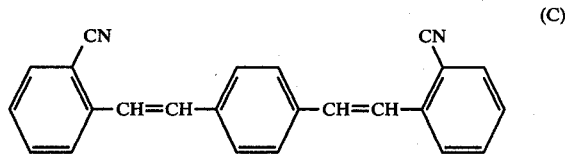

(C)

4 Claims, No Drawings

MIXTURES OF OPTICAL BRIGHTENERS

This is a division of application Ser. No. 214,227, filed Dec. 8, 1980, now U.S. Pat. No. 4,380,514.

The present invention relates to a process for the preparation of unsymmetrically substituted compounds of the general formula I

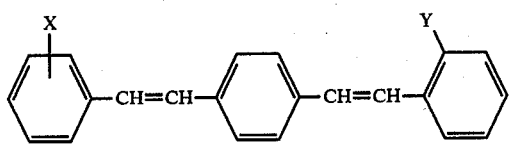

where X and Y independently of one another are hydrogen, fluorine, chlorine, cyano, $C_1$-$C_{10}$-alkoxycarbonyl, unsubstituted or substituted carbamyl or sulfamyl, a sulfonic acid aryl ester group, $C_1$-$C_{10}$-alkylsulfonyl or phenylsulfonyl, and at least one of X and Y is not hydrogen, and of mixtures of such optical brighteners, wherein terephthalaldehyde is reacted successively with a compound of the general formula IIa

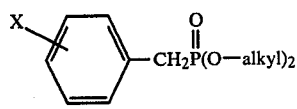

and a compound of the general formula IIb

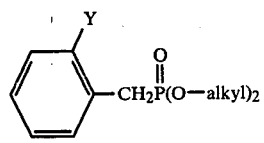

where X and Y have the meanings and alkyl is preferably $C_1$-$C_4$-alkyl, in the presence of an alkali, in a solvent from which the monocondensation product precipitates.

$COOCH_3$, $COOC_2H_5$, $COOC_3H_7$, $COOC_4H_9$, $COOC_6H_{13}$, $COOC_8H_{17}$,

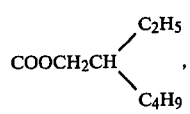

$COOC_{10}H_{21}$, $COOC_5H_{11}$, $CONHCH_3$, $CONHC_2H_5$, $CONHC_3H_7$, $CONHC_4H_9$, $CONHC_6H_{13}$, $CONHC_8H_{17}$, $CON(CH_3)_2$, $CON(C_2H_5)_2$, $CON(C_3H_7)_2$, $CON(C_4H_9)_2$,

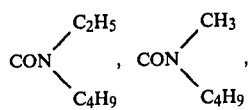

$CONHC_2H_4OH$, $CON(C_2H_4OH)_2$, $CONHC_2H_4OCH_3$, $CON(C_2H_4OCH_3)_2$, $CON(C_2H_4OC_4H_9)_2$,

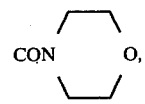

the corresponding sulfamyl radicals, $SO_2OC_6H_5$, $SO_2OC_6H_4CH_3$, $CH_3SO_2$, $SO_2C_2H_5$, $SO_2C_4H_9$, $SO_2C_6H_{13}$ and $SO_2C_8H_{17}$.

Suitable solvents for the reaction include, in particular, esters, ethers, hydrocarbons and chlorohydrocarbons, eg. ethyl acetate, n- and i-butyl acetate, methylglycol acetate, n- and i-propyl acetate, 1,2-dimethoxyethylene, diethylene glycol dimethyl ether, tetrahydrofuran, dioxane, toluene, xylene and chlorobenzene.

Preferred solvents are ethyl acetate, n- and i-butyl acetate, methylglycol acetate, tetrahydrofuran and dioxane.

The process according to the invention is advantageously carried out by dissolving the terephthalaldehyde in the solvent and then adding the compound of the formula IIa, followed by slow addition of the amount of alkali required for the condensation. After completion of the reaction, which can be followed by, for example, thin layer chromatography or gas chromatography, the compound of the formula IIb and the amount of alkali required for the latter are added. Advantageous reaction temperatures are from 30° to 50° C. whilst the total reaction time is as a rule from 6 to 12 hours.

Particularly suitable alkalis are alkali metal alcoholates, eg. sodium methylate, ethylate and butylate and potassium methylate, ethylate and butylate.

Details of the process according to the invention may be found in the Examples, where parts and percentages are by weight, unless stated otherwise.

Using the process according to the invention, it is possible to prepare compounds, and mixtures of compounds, of the general formula I, which do not contain any p,p'-isomers. The compounds and mixtures of compounds prepared according to the invention may be used as optical brighteners and exhibit particularly good fixing characteristics and a high brightening yield.

Mixtures of dicyano compounds, especially of o,m'-dicyano-bis-styrylbenzene and o,p'-dicyano-bis-styrylbenzene with o,o'-dicyano-bis-styrylbenzene, as well as mixtures of the o,m'-compound and o,p'-compound, are prepared. For instance, preferred mixtures are described in Examples 6, 24 and 25.

EXAMPLE 1

200 parts of 30% strength sodium methylate solution in methanol are added dropwise in the course of 4 hours to a mixture of 146 parts of 93% strength terephthalaldehyde, 275 parts of 93% strength diethyl o-cyanobenzylphosphonate and 1,200 parts of methylglycol acetate at 30°–35° C., with vigorous stirring. Stirring is continued for 4 hours at 30°–35° C. and 300 parts of 85% strength diethyl p-cyanobenzylphosphonate are then added. Thereafter, 306 parts of 30% strength sodium methylate solution are added dropwise in the course of 4 hours at 45°–50° C. Stirring is continued for 5 hours at the same temperature, the mixture is cooled to room temperature and the product is filtered off and washed thoroughly with methanol.

Yield: 260 parts of greenish yellow crystals (melting point 190°–192° C.) of the formula

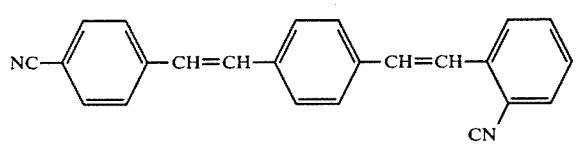

EXAMPLE 2

The procedure described in Example 1 was followed, but instead of 1,200 parts of methylglycol acetate, 1,400 parts of tetrahydrofuran were employed.

Yield of product (consisting of a single substance): 73%.

EXAMPLE 3

The procedure described in Example 1 was followed, but instead of 1,200 parts of methylglycol acetate, 1,100 parts of ethyl acetate were used.

Yield: as in Example 1.

EXAMPLE 4

The procedure followed was as in Example 1, but dioxane was used as the solvent.

Yield: 72%.

EXAMPLE 5

The procedure followed was as in Example 1, but isobutyl acetate was used as the solvent.

Yield: 78%.

EXAMPLE 6

2.34 parts of a 30% strength sodium methylate solution in methanol were added dropwise, in the course of 5 hours, to a mixture, stirred at 120 rpm, of 10 parts of methylglycol acetate, 1.4 parts of terephthalaldehyde and 3.3 parts of diethyl o-cyanobenzylphosphonate at 28°-32° C. After stirring for a further 4 hours at 40°-45° C., 1.9 parts of diethyl p-cyanobenzylphosphonate were added, and 1.7 parts of a 30% strength solution of sodium methylate in methanol were then introduced dropwise in the course of 6 hours at 35°-40° C. After stirring for a further 6 hours at 45°-50° C., the greenish white precipitate was filtered off.

Yield: 2.55 parts.

According to analysis by gas chromatography, the product is a mixture of

65% of 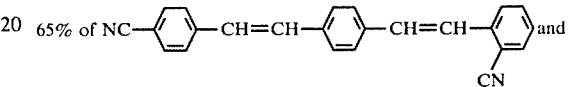 and

35% of 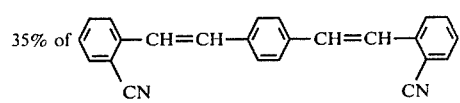

This mixture shows especially advantageous properties when used as a brightener for polyesters; in particular, its fixing capacity is exceptionally good for bis-styryl derivatives, and the brightening yield is high.

EXAMPLES 7-22

The procedure followed was similar to Example 1, except that the following solvents and phosphonates were used:

| Example | Solvent | Phosphonate ester II a | Phosphonate ester II b | Product |
|---|---|---|---|---|
| 7 | Dioxane | 2-NC-C$_6$H$_4$-CH$_2$P(O)(OC$_2$H$_5$)$_2$ | C$_6$H$_5$-CH$_2$P(O)(OC$_2$H$_5$)$_2$ | 2-NC-C$_6$H$_4$-CH=CH-C$_6$H$_4$-CH=CH-C$_6$H$_5$ |
| 8 | Ethyl acetate | 4-NC-C$_6$H$_4$-CH$_2$P(O)(OC$_2$H$_5$)$_2$ | " | 4-NC-C$_6$H$_4$-CH=CH-C$_6$H$_4$-CH=CH-C$_6$H$_5$ |
| 9 | Ethyl acetate | 2-NC-C$_6$H$_4$-CH$_2$P(O)(OC$_2$H$_5$)$_2$ | 2-(COOCH$_3$)-C$_6$H$_4$-CH$_2$P(O)(OC$_2$H$_5$)$_2$ | 2-NC-C$_6$H$_4$-CH=CH-C$_6$H$_4$-CH=CH-C$_6$H$_4$-2-COOCH$_3$ |
| 10 | Butyl acetate | 4-NC-C$_6$H$_4$-CH$_2$P(O)(OC$_2$H$_5$)$_2$ | 2-(COOC$_2$H$_5$)-C$_6$H$_4$-CH$_2$P(O)(OC$_2$H$_5$)$_2$ | 4-NC-C$_6$H$_4$-CH=CH-C$_6$H$_4$-CH=CH-C$_6$H$_4$-2-COOC$_2$H$_5$ |
| 11 | Butyl acetate | " | 2-(COOC$_4$H$_9$)-C$_6$H$_4$-CH$_2$P(O)(OC$_2$H$_5$)$_2$ | 4-NC-C$_6$H$_4$-CH=CH-C$_6$H$_4$-CH=CH-C$_6$H$_4$-2-COOC$_4$H$_9$ |
| 12 | Methylglycol acetate | " | 2-Cl-C$_6$H$_4$-CH$_2$P(O)(OC$_2$H$_5$)$_2$ | 4-NC-C$_6$H$_4$-CH=CH-C$_6$H$_4$-CH=CH-C$_6$H$_4$-2-Cl |
| 13 | Methylglycol acetate | " | 2-F-C$_6$H$_4$-CH$_2$P(O)(OC$_2$H$_5$)$_2$ | 4-NC-C$_6$H$_4$-CH=CH-C$_6$H$_4$-CH=CH-C$_6$H$_4$-2-F |
| 14 | Methylglycol acetate | " | 2,4-Cl$_2$-C$_6$H$_3$-CH$_2$P(O)(OC$_2$H$_5$)$_2$ | 4-NC-C$_6$H$_4$-CH=CH-C$_6$H$_4$-CH=CH-C$_6$H$_3$-2,4-Cl$_2$ |

| Example | Solvent | Phosphonate ester II a | Phosphonate ester II b | Product |
|---|---|---|---|---|
| 15 | Methylglycol acetate | " | 2,6-dichlorobenzyl-CH$_2$P(O)(OC$_2$H$_5$)$_2$ | NC–C$_6$H$_4$–CH=CH–C$_6$H$_4$–CH=CH–(2,6-Cl$_2$C$_6$H$_3$) |
| 16 | Ethylglycol acetate | 2-CN-benzyl-CH$_2$P(O)(OC$_2$H$_5$)$_2$ | 4-C$_4$H$_9$OOC-benzyl-CH$_2$P(O)(OC$_2$H$_5$)$_2$ | 2-CN-C$_6$H$_4$–CH=CH–C$_6$H$_4$–CH=CH–(2-COOC$_4$H$_9$-C$_6$H$_4$) |
| 17 | Ethylglycol acetate | " | 2-Cl-benzyl-CH$_2$P(O)(OC$_2$H$_5$)$_2$ | 2-CN-C$_6$H$_4$–CH=CH–C$_6$H$_4$–CH=CH–(2-Cl-C$_6$H$_4$) |
| 18 | Ethylglycol acetate | " | 2,4-Cl$_2$-benzyl-CH$_2$P(O)(OC$_2$H$_5$)$_2$ | 2-CN-C$_6$H$_4$–CH=CH–C$_6$H$_4$–CH=CH–(2,4-Cl$_2$-C$_6$H$_3$) |
| 19 | Ethylglycol acetate | " | 2-F-benzyl-CH$_2$P(O)(OC$_2$H$_5$)$_2$ | 2-CN-C$_6$H$_4$–CH=CH–C$_6$H$_4$–CH=CH–(2-F-C$_6$H$_4$) |
| 20 | Ethylglycol acetate | " | 4-CH$_3$-benzyl-CH$_2$P(O)(OC$_2$H$_5$)$_2$ | 2-CN-C$_6$H$_4$–CH=CH–C$_6$H$_4$–CH=CH–(4-CH$_3$-C$_6$H$_4$) |
| 21 | Tetrahydrofuran | 2-COOC$_2$H$_5$-benzyl-CH$_2$P(O)(OC$_2$H$_5$)$_2$ | 2-Cl-benzyl-CH$_2$P(O)(OC$_2$H$_5$)$_2$ | 2-COOC$_2$H$_5$-C$_6$H$_4$–CH=CH–C$_6$H$_4$–CH=CH–(2-Cl-C$_6$H$_4$) |
| 22 | Tetrahydrofuran | " | 4-Cl-benzyl-CH$_2$P(O)(OC$_2$H$_5$)$_2$ | 2-COOC$_2$H$_5$-C$_6$H$_4$–CH=CH–C$_6$H$_4$–CH=CH–(4-Cl-C$_6$H$_4$) |

-continued

| Example | Solvent | Phosphonate ester II a | Phosphonate ester II b | Product |
|---|---|---|---|---|
| 23 | Ethylglycol acetate | 2-CN-C6H4-CH2P(O)(OC2H5)2 | 3-CN-C6H4-CH2P(O)(OC2H5)2 | 2-NC-C6H4-CH=CH-C6H4-CH=CH-C6H4-3-CN |

EXAMPLE 24

20.3 parts of a 30% strength sodium methylate solution in methanol are added dropwise, in the course of 5 hours, to a mixture, stirred at 120 rpm, of 100 parts of methylglycol acetate, 14.4 parts of terephthalaldehyde and 28.6 parts of diethyl o-cyanobenzylphosphonate at 28°–32° C. The mixture is then stirred for 4 hours at 40°–45° C., 15.2 parts of diethyl m-cyanobenzyl phosphonate followed by 10.8 parts of 30% strength sodium methylate solution in methanol are then added, and the batch is stirred for 1 hour at 35° C. 6.8 parts of diethyl p-cyanobenzylphosphonate and a further 5 parts of 30% strength sodium methylate solution are then added, followed by stirring for 5 hours at 35°–40° C.

On working up the mixture as described in Example 6, a greenish white crystalline product is obtained, which according to analysis by gas chromatography contains

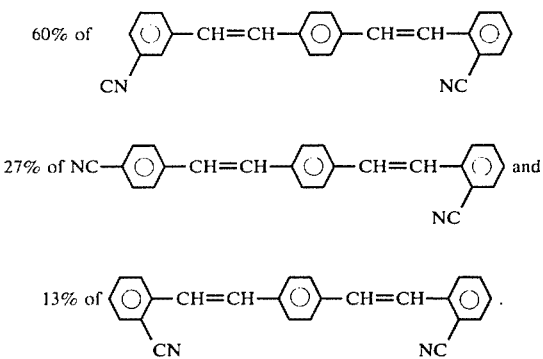

This mixture is an excellent brightener for polyester fabrics and in particular shows good fixing properties, a reddish tint and a good brightening yield.

EXAMPLE 25

The procedure described in Example 24 is followed, 14.4 parts of terephthalaldehyde being reacted successively with 25 parts of diethyl o-cyanobenzylphosphonate, 15.2 parts of diethyl m-cyanobenzylphosphonate and 10 parts of diethyl p-cyanobenzylphosphonate. A brightener mixture containing

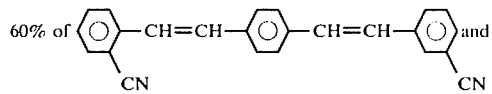

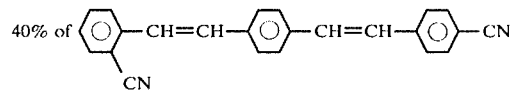

is obtained; this mixture is also an excellent brightener for polyesters.

I claim:

1. A mixture of optical brightener compounds consisting of a compound of formula (A)

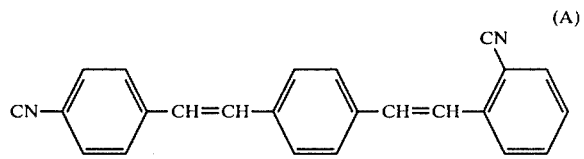

and at least one compound of formula (B) or (C) where formula (B) is

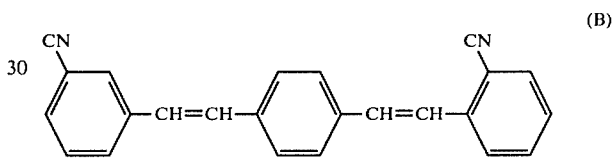

and formula (C) is

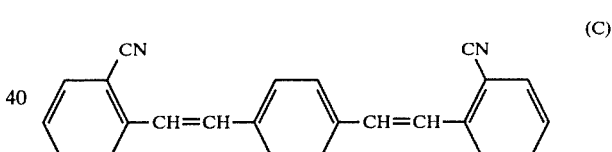

2. A mixture according to claim 1 of 65% of a compound of formula (A) and 35% of a compound of formula (C).

3. A mixture according to claim 1 of 60% of a compound of formula (B), 27% of a compound of formula (A) and 13% of a compound of formula (C).

4. A mixture according to claim 1 of 60% of a compound according to formula (B) and 40% of a compound according to formula (A).

* * * * *